US009815703B2

(12) United States Patent
Knauf et al.

(10) Patent No.: US 9,815,703 B2
(45) Date of Patent: Nov. 14, 2017

(54) METHOD FOR STARTING UP AND SHUTTING DOWN A PHOSGENE GENERATOR

(71) Applicant: Covestro Deutschland AG, Leverkusen (DE)

(72) Inventors: Thomas Knauf, Dormagen (DE); Andreas Karl Rausch, Kaarst (DE); Dirk Manzel, Moers (DE); Charles Bjoerndahl, Aukrug/Boken (DE); Matthias Ehlers, Marne (DE); Carlos Alvarez Herrero, Tarragona (ES); Francisco Munoz Velasco, Tarragona (ES)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 15/112,261

(22) PCT Filed: Jan. 16, 2015

(86) PCT No.: PCT/EP2015/050738
§ 371 (c)(1),
(2) Date: Jul. 18, 2016

(87) PCT Pub. No.: WO2015/110353
PCT Pub. Date: Jul. 30, 2015

(65) Prior Publication Data

US 2016/0340196 A1 Nov. 24, 2016

(30) Foreign Application Priority Data

Jan. 21, 2014 (EP) .................................... 14151884

(51) Int. Cl.

| | |
|---|---|
| ***C01B 31/28*** | (2006.01) |
| ***B01J 7/00*** | (2006.01) |
| ***B01J 19/00*** | (2006.01) |
| ***B01J 21/18*** | (2006.01) |
| ***C07C 263/10*** | (2006.01) |
| ***C07C 265/04*** | (2006.01) |
| ***C08G 64/06*** | (2006.01) |
| ***C08G 64/28*** | (2006.01) |

(52) U.S. Cl.
CPC ................ *C01B 31/28* (2013.01); *B01J 7/00* (2013.01); *B01J 19/0013* (2013.01); *B01J 21/18* (2013.01); *C07C 263/10* (2013.01); *C07C 265/04* (2013.01); *C08G 64/06* (2013.01); *C08G 64/28* (2013.01); *B01J 2219/00051* (2013.01)

(58) Field of Classification Search
CPC ..................................................... C01B 31/28
USPC ................................................. 528/196, 198
See application file for complete search history.

(56) References Cited

U.S. PATENT DOCUMENTS

| | | | |
|---|---|---|---|
| 3,331,873 | A | 7/1967 | De Long et al. |
| 3,960,761 | A | 6/1976 | Burger et al. |
| 4,231,959 | A | 11/1980 | Obrecht |
| 4,764,308 | A | 8/1988 | Sauer et al. |
| 6,399,823 | B1 | 6/2002 | Via et al. |
| 6,900,348 | B1 | 5/2005 | Reif et al. |
| 6,916,953 | B2 | 7/2005 | Walsdorff et al. |
| 6,930,202 | B1 | 8/2005 | Heuser et al. |
| 7,368,595 | B2 | 5/2008 | Wershofen et al. |
| 7,442,835 | B2 | 10/2008 | Keggenhoff et al. |
| 8,993,803 | B2 | 3/2015 | Olbert et al. |
| 2009/0143619 | A1 | 6/2009 | Kauth et al. |

FOREIGN PATENT DOCUMENTS

FR 2109186 A5 5/1972

OTHER PUBLICATIONS

Ullmann's Encyclopedia of Industrial Chemistry, 5th ed. vol. A 19p 413f., VCH Verlagsgesellschaft mbH, Weinheim, 1991.
Mitchell et al.: Selection of carbon catalysts for the industrial manufacture of phosgene; Catal. Sci. Technol., 2012, 2109-2115.
E. Wygasch in "Ullmann's Encyklopaedie der Technischen Chemie", Urban & Schwarzenberg, Munich 13 (1962) 493.

*Primary Examiner* — Terressa Boykin
(74) *Attorney, Agent, or Firm* — Donald R. Palladino

(57) ABSTRACT

The present invention relates to a method for operating a phosgene generator for producing phosgene by reacting carbon monoxide with chlorine in the gas phase on an activated carbon catalyst arranged in a reaction chamber, in which method, after a predefinable operating period, the phosgene production is at least temporarily interrupted by shutting down the phosgene generator over a shutdown period and, after a predefinable downtime, is resumed by starting up the phosgene generator over a start-up period, wherein the method is characterized in that the activated carbon catalyst, before the phosgene generator is started up, is freed of chlorine by adding carbon monoxide so that, during the start-up period, a maximum concentration of chlorine in the gas stream immediately downstream of the reaction chamber of 1000 ppmv is not exceeded. The invention also relates to the use of the phosgene thus obtained in the production of polycarbonate and isocyanates.

20 Claims, No Drawings

METHOD FOR STARTING UP AND SHUTTING DOWN A PHOSGENE GENERATOR

CROSS-REFERENCE TO RELATED APPLICATIONS

This application is a National Phase Application of PCT/EP2015/050738, filed Jan. 16, 2015, which claims priority to European Application No. 14151884.5, filed Jan. 21, 2014, each of which being incorporated herein by reference.

FIELD

The present invention relates to a method of operating a phosgene generator for preparing phosgene by reaction of carbon monoxide with chlorine in the gas phase over an activated carbon catalyst which is arranged in a reaction space in which the preparation (phosgene is at least temporarily interrupted after a prescribeable period of operation by running down the phosgene generator over a running-down time and, after a prescribeable stoppage time, recommenced by starting up the phosgene generator over a start-up time.

BACKGROUND

Phosgene is employed in many fields of chemistry, either as auxiliary or as intermediate. The largest field of use in terms of quantity is the preparation of diisocyanates as starting materials for polyurethane chemistry. Particular mention may be made in this respect of the materials tolylene 2,4- and 2,6-diisocyanate (TDI), the isomers and homologues of diphenylmethane diisocyanate (MDI) and hexamethylene diisocyanate (HDI).

The industrial preparation of phosgene from carbon monoxide and chlorine is known from the prior art (e.g. Ullmann's Encyclopedia of Industrial Chemistry, 5th ed. Vol. A 19p 413f., VCH Verlagsgesellschaft mbH, Weinheim, 1991). Here, carbon monoxide is combined in a stoichiometric excess with chlorine and passed over a fixed-bed catalyst. For industrial purposes, activated carbon is used as catalyst, and to this day the selection of a suitable activated carbon is carried out empirically (Mitchell et al.: Selection of carbon catalysts for the industrial manufacture of phosgene; Catal. Sci. Technol., 2012, 2, 2109-2115).

The activated carbon is consumed as time goes on and has to be renewed at regular intervals. Possible ways of regenerating the activated carbon catalyst have been proposed by E. Wygasch in "Ullmann's Encyklopädie der Technischen Chemie", (Urban & Schwarzenberg, Munich, 13 (1962) 493), with the reactivation of the activated carbon being carried out at temperatures of from 550° C. to 630° C.

In the preparation of phosgene, the purity of the starting materials carbon monoxide and chlorine has to meet demanding requirements for reasons of plant safety and for reasons of product quality. The starting materials should have low contents of methane and hydrogen since these can lead to a strongly exothermic reaction when combined with chlorine. The temperature rise can lead to a dangerous reaction between chlorine and the material of the apparatus, known as a chlorine-iron fire.

The starting materials should have low contents of sulfur, bromine and iodine since these can remain in the phosgene produced and can lead to a deterioration in quality when the phosgene is used in a downstream process such as the preparation of isocyanates. Such a deterioration in quality is, for example, a poorer color of the end product.

Processes for preparing phosgene having a low content of by-products are known from the prior art. For example, contents of less than 150 ppm of carbon tetrachloride are achieved by means of suitable process conditions (EP 1 135 329 B1), or chlorine containing less than 50 ppm (EP 118 78 08 B1), or less than 400 ppm (EP 152 90 33 B1), of free or bound bromine or iodine is required as starting material.

EP 1 808 430 B1 discloses a process for preparing isocyanates, in which phosgene containing less than 100 ppm of sulfur in elemental or bound form is used.

The formation of phosgene is a strong exothermic reaction having an enthalpy of formation of −107.6 kJ/mol. Phosgene formed is subject to a dissociation equilibrium and decomposes back into the starting materials at elevated temperatures. At 100° C., phosgene dissociates to such an extent that it contains about 50 ppm of chlorine.

Residual contents of chlorine in the phosgene produced interfere in virtually all possible uses of this intermediate. In order to keep the chlorine content of the phosgene produced as low as possible, firstly carbon monoxide is used in excess and, secondly, the phosgene formation reaction is completed at the lowest possible temperatures.

For this reason, carbon monoxide is used in an excess of from 3% by volume to 10% by volume over the stoichiometrically required amount in the preparation of phosgene. The carbon monoxide used in excess cannot be recycled and represents a loss of material. For this reason, many efforts have been made in the past to develop more economical processes for preparing phosgene. Thus, EP 2 067 742 A1 describes a process for preparing phosgene with reduced CO emission or reduced CO losses by means of a main combining, a subsequent condensation of the phosgene and a subsequent after-combining of the residual gas with chlorine. A process having a regulating concept for minimizing the CO excess is presented in WO 2010/103029 A1.

A further important aspect in the preparation of phosgene is the safe and uniform removal of the heat of reaction. This is achieved, for example, by the reaction being carried out in a shell-and-tube reactor, known as the phosgene generator, in the tubes of which the activated carbon is located and around which reaction tubes a cooling medium is circulated by forced convection or natural convection and partially vaporized there. EP 0 134 506 B1 describes a process in which the cooling can be utilized for generating steam. In such shell-and-tube reactors, the phosgene formation reaction between carbon monoxide and chlorine over suitable activated carbon catalysts already proceeds at about 40° C.-50° C., with the temperature in the catalyst filling in the tubes being able to rise to about 600° C. and, depending on the intensity of the cooling employed, dropping back to 40° C.-150° C. by the reactor outlet.

Cooling the catalyst bed to below 100° C. is also known, since phosgene having residual contents of chlorine of less than 50 ppm can then be obtained. For many fields of application, for example the production of isocyanate for polyurethane production, such a chlorine content represents the upper limit of the specification since otherwise deterioration in quality can occur. This is described, for example, in EP 0 134 506 B1. Such a deterioration in quality can be, for example, an increased content of chlorinated by-products or a poorer color of the end product.

To avoid such a deterioration in quality in isocyanate production, it is therefore necessary to avoid both the stoichiometric excess of carbon monoxide and also elevated reactor exit temperatures at the phosgene generator at all times.

Although the above-described processes of the prior art are able to produce a phosgene which does not lead to any deterioration in quality of the end products, only processes in normal operation are described. Start-up processes until a stable operating state at the desired load (known as "start-up time") or running-down processes until complete shutdown is attained (known as "running-down time") are not taken into account. However, studies which have led to the present invention have shown that increased amounts of chlorine can be formed during the start-up and running-down time, and these get into the product stream.

SUMMARY

It is therefore an object of the present invention to provide a process of the type mentioned at the outset which allows the production of phosgene having a low content of chlorine even during the start-up time. The process should preferably make it possible to produce phosgene having a content of chlorine of not more than 100 ppmv at the outlet from the phosgene generator.

This object is achieved by a method of operating a phosgene generator for preparing phosgene by reaction of carbon monoxide with chlorine in the gas phase over an activated carbon catalyst which is arranged in a reaction space in which the preparation of phosgene is at least temporarily interrupted after a prescribeable period of operation by running down the phosgene generator over a running-down time and, after a prescribeable stoppage time, recommenced by starting up the phosgene generator over a start-up time, where the process is characterized in that the activated carbon catalyst is freed of chlorine before starting up the phosgene generator by introduction of carbon monoxide to such an extent that a maximum concentration of chlorine in the gas stream immediately downstream of the reaction space of 1000 ppmv is not exceeded during the start-up time.

DETAILED DESCRIPTION

The present invention is based on the recognition that displacement of chlorine present in the activated carbon catalyst and the reactor periphery surrounding the latter can be carried out in a satisfactory way by the phosgene generator being flushed (blanketed) with carbon monoxide and the activated carbon catalyst thus being treated in a suitable manner. The activated carbon catalyst and the reactor periphery surrounding the latter is thus freed of chlorine before the process is started up and before carbon monoxide and especially chlorine are once again introduced into the phosgene generator during the course of the start-up. Here, in particular, the chlorine which is bound to the activated carbon is also displaced in a suitable manner. The treatment of the activated carbon can, for example, be carried out, a) before the start-up time and/or b) during the running-down time and/or c) after the running-down time. These methods can be realized in various ways, which are explained in detail below.

For the purposes of the present invention, the unit "ppmv" means parts per million by volume and is based on a temperature of 298.15 K and a pressure of 1013 hPa. The volume concentration of chlorine in a phosgene-containing gas stream can be determined, for example, UV-spectrometrically.

The unit standard cubic meters describes the amount of gas which would occupy a gas volume of one cubic meter under prescribed conditions (temperature, pressure, atmospheric humidity). For the purposes of the present invention, the standard cubic meter is based on a pressure of 1013.25 hPa, an atmospheric humidity of 0% (dry gas) and a temperature of 273.15 K (tn=0° C.) (standard conditions in accordance with DIN 1343, STPD).

The chlorine used for the reaction can be prepared by conventional industrial processes such as chloralkali or hydrogen chloride electrolysis and should be very pure. Chlorine having a purity of greater than 98% is particularly suitable. Preference is given to using liquid chlorine from a storage vessel, which is vaporized in a heated gasifier and subsequently freed of any entrained, liquid chlorine in an after-vaporizer.

The carbon monoxide used for the reaction can be prepared by conventional methods, for example from natural gas/naphtha in a synthesis gas plant or from coke by blowing-through oxygen. It has been found to be particularly advantageous for the carbon monoxide to have a methane content of less than 50 ppm.

As carbon catalyst, preference is given to using activated carbon. A granular activated carbon having a particle diameter of from about 3 to 10 mm, preferably from 3.5 to 7 mm, is preferably utilized as catalyst. The pore surface area of the activated carbon is preferably approximately 1000 $m^2/g$. The bulk density of the activated carbon used is preferably about 450 g/l. Possible activated carbons are, in particular, grades which have a compressive strength of more than 18 kp (determined by the method in DE-B 2 322 706, column 6, lines 28-38) and a benzene absorption capacity of more than 40% by weight. For example, the fracture- and abrasion-resistant activated carbons which conform to these conditions and have a high long-term heat resistance in accordance with DE-B 2 322 706 are well-suited.

Start-up and running-down times frequently occur as everyday events in industrial phosgene production and are not necessarily associated with opening or other mechanical ingress into the phosgene generator, but merely with shutdown and renewed start-up of phosgene production. These start-up and running-down times are in practice characterized by fluctuations in the carbon monoxide excess and residual contents of chlorine in the phosgene being able to occur. This is observed particularly when the gas flow is very small compared to the gas flow at full load. These residual contents of chlorine are disadvantageous since residual chlorine contents of max. 50 ppmv are required for the subsequent use, in particular for the preparation of isocyanates.

In a preferred further development of the method of the invention, a maximum concentration of chlorine in the gas stream immediately downstream of the reaction space of 100 ppmv, in particular 50 ppmv, is not exceeded, with a concentration of 10 ppmv preferably not being exceeded.

In a preferred embodiment of the method of the invention, the introduction of chlorine is reduced or directly interrupted over the running-down time in order to adhere to the maximum concentration of chlorine during running-down of the phosgene generator, with the introduction of carbon monoxide being maintained until the concentration of chlorine has reached or goes below the maximum concentration. This can be a period of a number of hours, for example 3 or 5 hours. This makes it possible to prevent an increased chlorine concentration from occurring in the phosgene stream during running-down. Likewise, an increase in the chlorine concentration in the generator, which on renewed start-up could lead to an increased chlorine concentration in the product stream, is prevented.

Here, the activated carbon catalyst can be maintained at a temperature of from 60° C. to 140° C. during the running-down time, as a result of which the rate of reaction of chlorine with carbon monoxide is kept at a high level.

As an alternative to or in addition to the abovementioned variant of the method, establishment of an increased chlorine concentration in the phosgene stream during start-up can also be prevented in a phosgene reactor whose operation has already been stopped. Here, the phosgene generator is in the stoppage time and, before it is started up, the introduction of carbon monoxide is commenced and a) the activated carbon catalyst is heated to a temperature of from 60° C. to 140° C. and/or b) the carbon monoxide gas stream is heated to a temperature of from 130° C. to 250° C., so that the chlorine still present on the activated carbon catalyst and/or in the reaction space from the previous production cycle reacts until the concentration thereof reaches or goes below the maximum concentration.

In a particularly preferred embodiment of the method of the invention, the amount of carbon monoxide used for reaching or going below the maximum concentration of chlorine is at least 40 standard cubic meters per metric ton of activated carbon catalyst in the reaction space, in particular at least 60 standard cubic meters per metric ton, preferably at least 80 standard cubic meters per metric ton.

For the purposes of the present invention, the commencement of the start-up of the phosgene generator can be defined by the commencement of introduction of chlorine. To ensure that the catalyst has a sufficient activity before the introduction of chlorine is commenced, the activated carbon catalyst can be heated to a temperature of at least 140° C., in particular at least 180° C.

The introduction of chlorine can be increased to a desired end value over the start-up time, with the increase being carried out, in particular, in steps and the steps preferably being 25%, 50%, 75% and 100% of the desired end value and/or the stepwise increase preferably being carried out at equal time intervals. A person skilled in the art will know that a continuously operated industrial process cannot be instantly run up to the process parameters before stoppage of production when starting from a production plant which is not in operation (e.g. after a brief stoppage). Starting materials and apparatuses have to be heated up, apparatuses may have to be made inert, the introduction of the starting materials into the apparatuses is gradually increased to the desired value. When a production plant for preparing phosgene is to be operated at an intended throughput M'intended of x [$m^3$(chlorine)/h], this intended throughput can, for example, be achieved by firstly setting the throughput M' to a value of 0.25 x at the commencement of phosgene production and the throughput then being increased via the intermediate steps M'=0.50 x and M'=0.75 x over a period of 4 hours to the value M'=x=M'intended. As an alternative, a continuous increase in load up to M'=x can also be carried out from a particular initial value, e.g. M'=0.50 x. M'intended of phosgene production depends on the consumer of the phosgene since a low phosgene content in the plants is always sought. These examples are naturally only illustrative of many possible start-up procedures, the precise configuration of which depends on the specific circumstances of a production plant and therefore cannot be generalized. However, a feature common to all conceivable start-up procedures is that the desired intended throughput of x is attained only after a period of time t has elapsed. This period of time t is referred to as start-up time for the purposes of the invention. The controlled increase in the introduction of chlorine over the start-up time makes it possible to avoid peaks in the chlorine concentration, which could possibly not react in good time and thus otherwise get into the product stream.

In a further preferred procedure, a molar excess of CO over chlorine of from 2 mol % to 20 mol %, in particular from 3 mol % to 15 mol %, can be set during the start-up time and the period of operation in the method of the invention.

The present invention further provides for the use of phosgene obtained by the method of the invention in the preparation of polycarbonate and isocyanates. Owing to the low content of chlorine, this phosgene can be used without prior treatment, in particular without a separate chlorine removal step, for isocyanate production.

The actual preparation of phosgene can in principle be carried out by all methods known from the prior art. To carry out this step of the method of the invention, it is possible to use a "cold combiner" as described in EP 1 640 341 B1 and a "hot combiner" as described in EP 0 134 506 B1. The contents of these patents are fully incorporated by reference into the present patent application.

In the case of cold combining, carbon monoxide and chlorine are reacted in the presence of elemental carbon at a temperature of from 30° C. to 80° C. and a pressure of from 120 kPa abs. to 400 kPa abs., measured directly downstream of the phosgene generator, in order to produce phosgene. In this method, it is possible to use conventional tube reactors made of normal steel or stainless steel, the tubes of which are filled with the carbon catalyst. The tube reactor can be operated continuously or discontinuously.

Carbon monoxide and chlorine are introduced in approximately equal parts, for example at room temperature, into the reactor. To ensure that the entire chlorine is reacted, it is possible to use a small excess of carbon monoxide. The two reactants are preferably mixed in a suitable mixing apparatus, e.g. a static mixer, before entry into the reactor. In this method, it is advantageous that no specific pretreatment of the catalyst is necessary.

The temperature of the gas stream leaving the reactor should not exceed 80° C., measured directly downstream of the phosgene generator, with the temperature of the gas stream leaving the reactor preferably being in the range from 40° C. to 70° C. To adhere to these desired temperatures, it is possible to provide an appropriate cooling apparatus by means of which the heat of reaction liberated during the reaction is removed and overheating of the catalyst is prevented.

The pressure directly downstream of the phosgene generator is preferably not more than 300 kPas abs. In this way, it is ensured that no phosgene condenses in the reactor.

The phosgene exiting at the top of the reactor is preferably condensed at temperatures from −10° C. to −20° C.

In the case of so-called hot combining (described, for example, in EP 0 134 506 B1) phosgene is prepared by reaction of chlorine with carbon monoxide in tube reactors containing activated carbon as catalyst with simultaneous utilization of the heat of reaction arising to generate steam. Here, from 95% by volume to 98% by volume of the chlorine used is reacted with excess carbon monoxide at reaction temperatures of above 250° C. in a first tube reactor which contains granulated activated carbon and has an internal tube diameter of not more than 100 mm in order to form phosgene. The heat of reaction arising here is removed by evaporative cooling by means of a liquid which boils at from 150° C. to 320° C. or by means of a non-boiling liquid whose temperature at the reactor outlet is maintained at from 150° C. to 320° C. by means of forced circulation pumps and temperature control. The liquid or gaseous heat transfer medium leaving the reactor is condensed in a heat exchanger supplied with water as cooling medium with generation of steam and/or cooled to a temperature below the temperature of the heat transfer medium at the reactor outlet and recirculated to the reactor. The reaction gases leaving the reactor are cooled to a temperature of from 50° C. to 120° C. and subsequently introduced into a second reactor which contains granulated activated carbon and whose temperature is thermostatically set to from 50° C. to 100° C. and in which the reaction is completed, so that the phosgene leaving the second reactor has a residual chlorine content of less than 50 ppmv. The subsequent condensation of the phosgene is carried out in the manner described above.

The method of the invention can, for example, be operated in the following way:

a) chlorine and carbon monoxide are reacted in the presence of an activated carbon catalyst in a shell-and-tube reactor containing a plurality of reaction tubes and a coolant space surrounding the reaction tubes, using chlorine and carbon monoxide in a molar excess of CO of from 2% to 20% and with the amount M' of the chlorine-containing stream (a.1) fed into the phosgene generator subsequently increased over a period of $t_1$ from the commencement of phosgene production until a prescribed intended value for M' is attained;
b) the heat of reaction arising in step a) is removed by evaporative cooling by means of a liquid which boils at from 150° C. to 320° C. or by means of a non-boiling liquid whose temperature at the reactor outlet is maintained at 150° C.-320° C. by means of forced circulation pumps and temperature control;
c) The reaction gases obtained in step a) are cooled to a temperature of from 50° C. to 120° C. on leaving the reactor (1) and
d) introduced into a second reactor (2) which contains granulated activated carbon and whose temperature is thermostated to from 50° C. to 100° C. and in which the reaction is completed, so that the phosgene leaving the second reactor has a residual chlorine content of less than 100 ppmv.

This occurs as a result of a carbon monoxide stream (a.2) being introduced into the reactor (1) at least during a period of time to before commencement of the start-up process for phosgene production so that this stream displaces or consumes chlorine which is present.

For the purposes of the present invention, the content of chlorine, free in the reactor space or bound on the activated carbon catalyst, should be brought to a very low value before the actual start-up, which commences with the introduction of chlorine. This objective can be achieved in alternative ways, for example:

a) The plant is brought by means of industrial heating to operating temperature while being blanketed with carbon monoxide (a.2) and without chlorine (a.1) before commencement of a new production cycle, i.e. before the introduction of chlorine (a.1) and carbon monoxide (a.2). At the earliest as soon as the phosgene generator has attained the desired temperature of at least 140° C., preferably at least 180° C., phosgene production is started by introduction of chlorine.
b) After the end of a production cycle, i.e. after the introduction of chlorine (a.1) has been stopped and the residual amounts of phosgene still present in the production plant, the carbon monoxide flow (a.2) is reduced to a smaller flow and maintained for a certain period of time before the process for the preparation of phosgene is finally shut down. In the blanketing with carbon monoxide, the residual heat of the industrial heating and the activated carbon catalyst is exploited. Thus, the amount of chlorine still adhering to the activated carbon after the continuous reaction has been shut down is minimized and cannot change the stoichiometry between carbon monoxide and chlorine during start-up.
c) A phosgene generator which has been shut down is blanketed exclusively with carbon monoxide. Here, either the phosgene generator can be heated by means of industrial heating or the carbon monoxide stream can be heated before it enters the phosgene generator, or both.

It is common to all embodiments that they reduce the content of chlorine, free in the reactor space or bound to the activated carbon catalyst. The degree of reduction achieved by the respective embodiment depends, in particular, on four factors:

amount of carbon monoxide during blanketing
temperature of the cooling jacket of the phosgene generator during blanketing
temperature of the carbon monoxide during blanketing
duration of blanketing An increase in one or more of the four factors leads to a greater reduction of the content of free or bound chlorine in the phosgene generator.

The amount of carbon monoxide for blanketing can be, for example, from 1 $m^3/h$ to 250 $m^3/h$, preferably from 5 $m^3/h$ to 100 $m^3/h$, particularly preferably from 10 $m^3/h$ to 50 $m^3/h$.

The temperature of the cooling jacket of the phosgene generator during blanketing can be from 20° C. to 250° C., preferably from 60° C. to 200° C., particularly preferably from 160° C. to 200° C.

The temperature of the carbon monoxide during blanketing can be from 20° C. to 250° C., preferably from 130° C. to 250° C., particularly preferably from 220° C. to 250° C.

The duration of blanketing is preferably at least 0.5 hours, preferably at least 2 hours, particularly preferably at least 6 hours. Blanketing times of a plurality of days can be employed for the purposes of the present invention and can be advantageous. The duration of blanketing and the amount of carbon monoxide are, in the case of this embodiment, to be combined in such a way that, based on the mass of the activated carbon catalyst, at least 40 standard cubic meters of CO per metric ton of activated carbon catalyst are used, preferably from 60 standard cubic meters and particularly preferably 80 standard cubic meters.

A suitable combination of the abovementioned factors also makes it possible to achieve positive effects when the activated carbon has been subjected to severe loading or when a breakthrough of chlorine has previously been recorded on the phosgene generator.

The procedures according to the invention result, inter alia, in the following advantages for the start-up time period in the preparation of phosgene:

i) Only the chlorine which is fed into the phosgene generator during start-up is available as reaction partner for carbon monoxide. Thus, the desired excess of carbon monoxide over chlorine is maintained.
ii) Temperature control in the phosgene generator is ensured precisely in its full scope. Local thermal overloading of the activated carbon catalyst is thus avoided. This increases the operating life thereof.

iii) Avoidance of excessively high content of free chlorine in the phosgene. There is thus reduced formation of chlorinated impurities (e.g. chlorination of solvent or isocyanate) in the subsequent use of the phosgene. In the case of isocyanate production, this leads to an improvement in color.

The method of the invention thus allows, as a result of a low content of chlorine in the phosgene generator before the actual commencement of phosgene production, start-up of the phosgene generator and subsequent use of the resulting phosgene in a technically smooth manner without downtime with immediately higher final product quality of the desired product, e.g. isocyanates.

The phosgene which has been prepared according to the method of the invention and leaves the top of the reactor is preferably condensed at temperatures of from −10° C. to −45° C. It can be used directly without further purification for preparing polycarbonates or for preparing isocyanates from amines such as methylenedi(phenylamine), polymethylenepolyphenylpolyamine, mixtures of methylenedi(phenylamine) and polymethylenepolyphenylpolyamine, tolylenediamine, xylylenediamine, hexamethylenediamine, isophoronediamine and naphthyldiamine, with preference being given to methylenedi(phenylamine), mixtures of methylenedi(phenylamine) and polymethylenepolyphenylpolyamine and also tolylenediamine, or for preparing pharmaceutical active compounds or for preparing active compounds for crop protection.

The present invention will be illustrated below with the aid of working examples.

EXAMPLES

Contents indicated in ppmv or % are proportions by volume based on the total volume of the respective material (stream). Analytical values of the chlorine contents were, unless indicated otherwise, determined by means of UV spectrometry.

Specifications of the Carbon Monoxide and Chlorine Used:

Carbon monoxide should have a purity of at least 96% by volume, and chlorine should have a purity of at least 98% by volume, with the following contents of impurities not being exceeded:

In carbon monoxide:

| Test feature | | Specification | Measurement unit |
|---|---|---|---|
| Carbon monoxide | (CO) | min. 96.0 | % by volume |
| Ammonia | ($NH_3$) | max. 100 | mg/standard $m^3$ |
| Total sulfur | (S) | max. 10 | mg/standard $m^3$ |
| Methane | ($CH_4$) | max. 500 | ppm by volume |
| Oxygen | ($O_2$) | max. 0.5 | % by volume |
| Water | ($H_2O$) | max. 100 | ppm by volume |
| Hydrogen | ($H_2$) | max. 2 | % by volume |

In chlorine

| Test feature | | Specification | Measurement unit |
|---|---|---|---|
| Chlorine | ($Cl_2$) | min. 98.0 | % by volume |
| Carbon dioxide | ($CO_2$) | max. 1 | % by volume |
| Oxygen | ($O_2$) | max. 1 | % by volume |
| Nitrogen | (Na) | max. 1 | % by volume |
| Water | ($H_2O$ | max. 64 | mg/standard $m^3$ |

General Conditions for the Preparation of Phosgene in a "Run-in" Production Plant (i.e. after the Start-Up Time t has Elapsed) for Cold Combiner In a mixing tube, 810 standard $m^3$/h of chlorine and 955 standard $m^3$/h of carbon monoxide are mixed continuously at 19° C. and a pressure of 1.8 bar absolute. An excess of carbon monoxide over chlorine is used, so that 9% of carbon monoxide still remain in the phosgene after complete reaction of the chlorine. The mixed gas composed of chlorine and carbon monoxide is fed into a distributor located at the bottom of a shell-and-tube phosgene generator. 2 metric tons of activated carbon (Norit RB4C) are present as catalyst in the tubes above the distributor. The mixed gas reacts over this catalyst in a strong exothermic reaction to form phosgene. The reaction is cooled by means of evaporative water cooling using a water circuit. The temperature of the phosgene in the outlet line from the generator is 55° C. and the pressure is 1.53 bar absolute. At this point, the completeness of the reaction is monitored by continuously measuring the residual chlorine content and the carbon monoxide content. The gaseous phosgene prepared in this way, which contains excess carbon monoxide, is then condensed in a phosgene liquefier at −17° C. The bottom product on the phosgene liquefier runs into a phosgene solution tank. Excess carbon monoxide does not condense and is conveyed via the top into a downstream second phosgene generator having an identical construction and is treated there with an appropriate amount of chlorine so that, once again, 9% of carbon monoxide still remain in the phosgene after complete reaction of the chlorine. Downstream of the second phosgene generator, too, the completeness of the reaction is monitored by continuously measuring the residual chlorine content and the carbon monoxide content. The phosgene produced in this way is condensed in a second phosgene liquefier at −17° C. The bottom product from the second phosgene liquefier likewise runs into the phosgene solution tank. Excess carbon monoxide, which is accompanied by traces of phosgene, is conveyed as overhead product into an offgas manifold, freed of phosgene there and subsequently burned in a thermal exhaust air purification facility. Thus, 4.2 metric tons of phosgene per hour enter the phosgene solution tank.

In the phosgene solution tank, the phosgene can, if required, be mixed with a solvent. For a process for preparing isocyanates, the phosgene is mixed with monochlorobenzene in the phosgene solution tank to give a 35% strength phosgene solution and taken off at −2° C. for further use, e.g. the preparation of isocyanates. In other industrial processes, it can also be used as pure liquid phosgene.

General Conditions for the Start-Up of a Phosgene Generator

To obtain the nominal capacity of the plant ($M'_{intended}$), operation is firstly commenced with relatively small streams of chlorine and carbon monoxide (in examples 1 and 2, the plant is started at from 50 to 60% of the nominal capacity, corresponding to a production output of about 2.5 metric t/h (phosgene)).

After the start-up phase, these flows are increased to the desired intended load. The running-up of the production load can be effected manually or by means of an automatic start-up facility. The plant is in each case run as quickly as possible up to the desired intended load, with the phosgene formed during the start-up phase having a residual chlorine content of <100 ppm of chlorine at the output from the phosgene generator.

Example 1 (Comparative Example): Joints Introduction of Chlorine and CO Leads to 400 or 1000 ppm of Chlorine in Phosgene After repair work in the phosgene plant, the phosgene generator is started up by chlorine and carbon monoxide being introduced simultaneously into a mixing tube which has been made inert by means of nitrogen. The amount of the two starting materials introduced into the mixing tube during the start-up time t of 45 minutes is increased steplessly from 0 $m^3/h$ to 545 standard $m^3/h$ of carbon monoxide and steplessly from 0 $m^3/h$ to 455 standard $m^3/h$ of chlorine. A content of carbon monoxide of 9% in the phosgene is obtained after 45 minutes. The temperature in the mixing tube is 18° C., and a pressure of 1.8 bar absolute is established directly. The mixed gas composed of chlorine and carbon monoxide subsequently enters the interior of the shell-and-tube phosgene generator, which interior has a temperature of 18° C., and displaces the inert nitrogen. The reaction to form phosgene starts immediately and is strongly exothermic. The heat of reaction is removed by means of evaporative water cooling using a water circuit. The temperature of the phosgene in the output line from the generator is, after 5 minutes, 55° C. and the pressure is 1.53 bar absolute. At this point, the phosgene has a residual chlorine content of >100 ppm and a peak of >1000 ppm (above the measurement range of 1000 ppm) during the start-up phase The phosgene prepared in this way is, as described in the general production conditions, condensed and collected in the phosgene solution tank. After 45 minutes, these flows are increased to the desired intended load. The running-up of the plant can be effected manually or using an automatic start-up facility. The plant is in each case run up to the intended load as quickly as possible.

Phosgene having an increased chlorine content is obtained in the phosgene solution tank during the start-up phase since part of the chlorine is also condensed in the phosgene liquefier. The amount of chlorine in phosgene is diluted continuously to <50 ppm of chlorine in the end product phosgene by further phosgene over the course of a day. The use of this phosgene contaminated with chlorine leads for 12 hours to color problems in the phosgenation of MDA to the end product MDI. The color number of the MDI is >0.210 and the peak is at 0.240 (yellow value).

The color number (yellow value) was determined by dissolving 1.0 g of the isocyanate obtained in chlorobenzene and diluting it with chlorobenzene to 50 ml. The extinction relative to chlorobenzene was determined on this solution at a wavelength of 430 nm and a path length of 10 mm at room temperature. This method was employed for all reported figures for the yellow value.

Example 2 (According to the Invention): Initial Operation with CO Before Phosgene Production is Commenced by Introduction of Chlorine A phosgene plant is started up by carbon monoxide and chlorine being fed with a time offset of 1 minute into a mixing tube which has been made inert. The amount of the two starting materials introduced into the mixing tube during the start-up time t of 45 minutes, in the case of chlorine accordingly only 44 minutes, is increased steplessly from 0 $m^3/h$ to 545 standard $m^3/h$ of carbon monoxide and steplessly from 0 $m^3/h$ to 455 standard $m^3/h$ of chlorine. After 45 minutes a content of carbon monoxide of 9% in the phosgene is obtained. The temperature in the mixing tube is 18° C. and a pressure of 1.8 bar absolute is established directly. Carbon monoxide and, with a time offset, the mixed gas composed of chlorine and carbon monoxide enters the interior of the shell-and-tube phosgene generator, which interior has a temperature of 18° C., and displaces the inert nitrogen. The reaction to form phosgene starts immediately and is strongly exothermic. The heat of reaction is removed by means of evaporative water cooling using a water circuit. The temperature of the phosgene in the outlet line from the generator is, after 5 minutes, 55° C. and the pressure is 1.57 bar absolute. The phosgene prepared in this way is, as described in the general production conditions, condensed and collected in the phosgene solution tank. After 45 minutes, these flows are increased to the desired intended load. The running-up of the plant can be effected manually or using an automatic start-up facility. The plant is in each case run up as quickly as possible to the intended load, with the phosgene formed during the start-up phase having a residual content of 22 ppm, with this value being determined in the outlet line from the generator.

The use of this phosgene, which is contaminated with only traces of chlorine, in the phosgenation of MDA leads to an almost colorless end product MDI having a color number of 0.160 (yellow value).

General Conditions for the Preparation of Phosgene in a Run-in Production Plant (i.e. after the Start-Up Time $t_1$ has Elapsed) for Hot Combiner In a mixing tube, 3200 standard $m^3/h$ of chlorine and 4230 standard $m^3/h$ of carbon monoxide are mixed continuously at 20° C. and a pressure of 3.2 bar absolute. An excess of carbon monoxide over chlorine is used, so that 12% of carbon monoxide still remain in the phosgene after complete reaction of the chlorine. The mixed gas composed of chlorine and carbon monoxide is fed into a distributor located at the bottom of a shell-and-tube phosgene generator. Four metric tons of activated carbon (Norit RB4C) are present as catalyst in the tubes above the distributor. The catalyst is protected from discharge and trickling down by a mesh screen above and below the tube plate. The mixed gas reacts over this catalyst in a strongly exothermic reaction to form phosgene. The heat of reaction is transferred by means of evaporative cooling to a heat transfer oil (decalin), so that the temperature of the phosgene in the outlet line from the generator is 234° C. The pressure is 2.55 bar absolute. Owing to the high reaction temperature in the hot combiner, disproportionation occurs and 1-3% of chlorine are still present in the exiting gas stream.

In the outlet from the downstream gas cooler, the completeness of the reaction is monitored by continuously measuring the residual chlorine content and the content of carbon monoxide. The gaseous phosgene prepared in this way, which contains excess carbon monoxide and a small amount of chlorine, is then cooled down to 117° C. in a gas cooler and fed into a further shell-and-tube phosgene generator. In the second reactor, the chlorine present in the gas stream is reacted over a catalyst (activated carbon: Norit RB4C) to form phosgene. The reaction is cooled by means of evaporative cooling using a heat transfer medium (methylene chloride). The temperature of the phosgene in the outlet line from the second generator is 98° C. and the pressure is 2.46 bar absolute. The completeness of the reaction is likewise monitored in the outlet from the 2nd phosgene reactor by continuously measuring the residual chlorine content and the content of carbon monoxide.

The chlorine-free phosgene prepared in this way is condensed in a phosgene liquefier at −17° C. The bottom product from the phosgene liquefier runs into the phosgene reservoir of the phosgene absorption column. Excess carbon monoxide does not condense and is discharge at the top and treated in a mixing tube with an appropriate amount of chlorine, then reacted over activated carbon in a downstream third phosgene generator (after-combiner) having an identical construction to form phosgene. The reaction is cooled by means of evaporative cooling using a heat transfer medium (methylene chloride).

After complete reaction of the introduced chlorine, 2.5% of carbon monoxide still remain in the phosgene. Downstream of the third phosgene generator, too, the completeness of the reaction is monitored by continuously measuring the residual chlorine content and the content of carbon monoxide. The phosgene prepared in this way is partly condensed together with phosgene vapor from the phosgenation at −17° C. in a vapor condenser and discharged into the phosgene reservoir of the phosgene absorption column. The excess carbon monoxide is conveyed, together with the HCl gas formed in the phosgenation, as overhead product from the phosgene absorption into the HCl absorption. In a vapor condensation downstream of the HCl absorption, water vapor and HCl gas are condensed, leaving the excess carbon monoxide accompanied by traces of phosgene as tailgas. This gas stream is conveyed into an offgas manifold, freed of phosgene there and subsequently burned in a thermal exhaust air purification.

18 metric tons of phosgene per hour are prepared in this way and mixed with a solvent in the phosgene absorption. For a process for preparing isocyanates, the phosgene is mixed with monochlorobenzene in the phosgene absorption to give a 45% phosgene solution and taken off at −7° C. for further use, e.g. the preparation of isocyanates. In other industrial processes, it can also be used as pure liquid phosgene.

Example 3 (Comparative Example): Hot Operation: No Preliminary Stream of Carbon Monoxide During Heating-Up of the Generators After repair work in the phosgene plant, the phosgene generator is started up by feeding chlorine and carbon monoxide simultaneously into a mixing tube which has a volume of 100 liters and has been made inert by means of nitrogen. The amount of the two starting materials introduced into the mixing tube during the start-up time t of 30 minutes is increased steplessly from 0 standard $m^3$/h to 1000 standard $m^3$/h of carbon monoxide and steplessly from 0 standard $m^3$/h to 800 standard $m^3$/h of chlorine. After 30 minutes, a content of carbon monoxide in the phosgene of 11% is obtained. The temperature in the mixing tube is 20° C. and a pressure of 3.2 bar absolute is established directly. The mixed gas composed of chlorine and carbon monoxide subsequently enters the interior of the shell-and-tube phosgene generator, which interior has been preheated to 220° C., and displaces the inert nitrogen.

The reaction to form phosgene starts immediately and is strongly exothermic. The heat of reaction is removed by means of evaporative cooling using a heat transfer oil circuit (decalin). The temperature of the phosgene in the outlet line from the generator is, after 10 minutes, 234° C. and the pressure is 2.55 bar absolute. At this point, the phosgene has a residual chlorine content of >1000 ppm (above the measurement range of 1000 ppm) during the start-up phase. The phosgene produced in this way is, as described in the general production conditions, cooled down to 113° C. and introduced into the downstream shell-and-tube phosgene generator. Since the temperature of the reactor is only 30° C. at the beginning and the starting material concentration in the reaction gas is low, it takes about 5 minutes for the exothermic reaction to start. In the downstream second reactor, the chlorine and CO present in the phosgene produced is, as described in the general production conditions, reacted to form phosgene. In the outlet from the 2nd phosgene generator, the residual chlorine content is >1000 ppm (above the measurement range of 1000 ppm) during the start-up phase.

The phosgene which has been prepared in this way and condensed in the phosgene liquefier has an increased chlorine content during the start-up phase, since the chlorine is partly also condensed in the phosgene liquefier. The amount of chlorine in phosgene is diluted continuously to <50 ppm of chlorine in the end product phosgene by further phosgene over the course of a day. The use of this phosgene contaminated with chlorine leads for 18 hours to color problems in the phosgenation of MDA to form the end product MDI. The color number of the MDI is >0.200 and has a peak at 0.220 (yellow value).

Example 4 (According to the Invention): Hot Operation: CO Introduced During Heating-Up of the Generators A phosgene is started up by introducing carbon monoxide and chlorine with a time offset of 10 minutes into a mixing tube which has been made inert. The amount of the two starting materials introduced into the mixing tube during the start-up time t of 30 minutes, for chlorine accordingly only 20 minutes, is increased steplessly from 0 standard $m^3$/h to 1000 standard $m^3$/h of carbon monoxide and steplessly from 0 standard $m^3$/h to 800 standard $m^3$/h of chlorine. After 30 minutes, a content of carbon monoxide of 11% in the phosgene is obtained. The temperature in the mixing tube is 20° C. and a pressure of 3.2 bar absolute is established directly. The mixed gas composed of chlorine and carbon monoxide subsequently enters the interior of the shell-and-tube phosgene generator, which interior has been preheated to 220° C., and displaces the inert nitrogen.

The reaction to form phosgene starts immediately and is strongly exothermic. The heat of reaction is removed by means of evaporative cooling using a heat transfer oil circuit (decalin). The temperature of the phosgene in the outlet line from the generator is, after 10 minutes, 234° C. and the pressure is 2.55 bar absolute. At this point, the phosgene has a residual chlorine content of 100-800 ppm during the start-up phase. The phosgene prepared in this way is, as described in the general production conditions, cooled down to 113° C. In the downstream shell-and-tube phosgene generator, the remaining chlorine reacts in the presence of the CO excess to form phosgene.

The phosgene prepared in this way is, as described in the general production conditions, condensed and collected in the phosgene absorption. After 60 minutes, these flows are increased to the desired intended load. The running-up of the plant can be effected manually or using an automatic start-up facility. The plant is in each case run up as quickly as possible to the intended load, with the phosgene formed during the start-up phase having a residual chlorine content of 25 ppm. This measurement is carried out in the outlet line from the generator. The use of this phosgene, which is contaminated with only traces of chlorine, lead in the phosgenation of MDA leads to an almost colorless end product MDI having a color number of 0.170 (yellow value).

TABLE 1

Comparison of the results from the examples

| Example | Chlorine in phosgene [ppm] | Color number of the MDI [yellow value] |
|---|---|---|
| 1 (comparison) | >1000 | 0.240 |
| 2 (according to the invention) | 22 | 0.160 |
| 3 (comparison) | >1000 | 0.220 |
| 4 (according to the invention) | 25 | 0.170 |

As the examples show, phosgene having low chlorine contents which allows the preparation of virtually colorless MDI is formed only when the phosgene generator is started up according to the invention.

The invention claimed is:

1. A method of operating a phosgene generator for preparing phosgene by reacting carbon monoxide with chlorine in the gas phase over an activated carbon catalyst which is arranged in a reaction space, comprising at least temporarily interrupting the preparation of phosgene after a prescribeable period of operation by running down the phosgene generator over a running-down time and, after a prescribeable stoppage time, recommencing the preparation of phosgene by starting up the phosgene generator over a start-up time, wherein the activated carbon catalyst is freed of chlorine before starting up the phosgene generator by introducing carbon monoxide to such an extent that a maximum concentration of chlorine in the gas stream immediately downstream of the reaction space of 1000 ppmv is not exceeded during the start-up time.

2. The method of claim 1, wherein a maximum concentration of chlorine in the gas stream immediately downstream of the reaction space of 100 ppmv is not exceeded.

3. The method of claim 1, comprising reducing or directly interrupting the introduction of chlorine over the running-down time in order to adhere to the maximum concentration of chlorine during running-down of the phosgene generator, with the introduction of carbon monoxide being maintained until the concentration of chlorine has reached or gone below the maximum concentration.

4. The method of claim 3, comprising maintaining the activated carbon catalyst at a temperature of from 60° C. to 140° C. during the running-down time.

5. The method of claim 1, wherein the phosgene generator is in the stoppage time and, before it is started up, the introduction of carbon monoxide is commenced and comprising:

a) heating the activated carbon catalyst to a temperature of from 60° C. to 140° C. and/or b) heating the carbon monoxide gas stream to a temperature of from 130° C. to 250° C., so that the chlorine still present on the activated carbon catalyst and/or in the reaction space from the previous production cycle reacts until the concentration thereof reaches or goes below the maximum concentration.

6. The method of claim 5, wherein after the concentration of chlorine reaches or goes below the maximum concentration, the activated carbon catalyst is heated to a temperature of at least 140° C. before the introduction of chlorine is commenced.

7. The method of claim 1, wherein the amount of carbon monoxide used for reaching or going below the maximum concentration of chlorine is at least 40 standard cubic meters per metric ton of activated carbon catalyst in the reaction space.

8. The method of claim 1, wherein the commencement of the start-up of the phosgene generator is defined by the commencement of the introduction of chlorine.

9. The method of claim 1, wherein the introduction of chlorine is increased to a desired end value over the start-up time, with the increase being carried out in steps.

10. The method of claim 1, wherein the volume concentration of chlorine is determined UV-spectrometrically.

11. The method of claim 1, wherein a molar excess of CO over chlorine of from 2 mol % to 20 mol % is set during the start-up time and the period of operation.

12. The method of claim 2, wherein a maximum concentration of chlorine in the gas stream immediately downstream f the reaction space of 50 ppmv is not exceeded.

13. The method of claim 12, wherein a maximum concentration of chlorine in the gas stream immediately downstream of the reaction space of 10 ppmv is not exceeded.

14. The method of claim 6, wherein after the concentration of chlorine reaches or goes below the maximum concentration, the activated carbon catalyst is heated to a temperature of at least 180° C. before the introduction of chlorine is commenced.

15. The method of claim 7, wherein the amount of carbon monoxide used for reaching or going below the maximum concentration of chlorine is at least 60 standard cubic meters per metric ton of activated carbon catalyst in the reaction space.

16. The method of claim 15, wherein the amount of carbon monoxide used for reaching or going below the maximum concentration of chlorine is at least 80 standard cubic meters per metric ton of activated carbon in the reaction space.

17. The method of claim 9, wherein the increase is carried out ire steps of 25%, 50%, 75% and then 100% of the desired end value.

18. The method of claim 9, wherein the stepwise increase is d out at equal time intervals.

19. Polycarbonate prepared from phosgene obtained by the method of claim 1.

20. Isocyanates prepared from phosgene obtained by the method of claim 1.

* * * * *